United States Patent [19]

O'Boyle

[11] Patent Number: 4,544,329

[45] Date of Patent: Oct. 1, 1985

[54] PERISTALTIC PUMP HAVING A SPIRAL CAM AND STRAIGHT PERISTALTIC TUBE

[75] Inventor: Matthew O'Boyle, Somers, Conn.

[73] Assignee: Windsor Medical, Inc., Enfield, Conn.

[21] Appl. No.: 458,060

[22] Filed: Jan. 14, 1983

[51] Int. Cl.[4] .................. F04B 43/12; F04B 45/08
[52] U.S. Cl. ...................................... 417/53; 417/474; 417/475
[58] Field of Search ............... 417/477, 476, 475, 474, 417/53; 418/45, 220, 153

[56] References Cited

U.S. PATENT DOCUMENTS 2,621,605 12/1952 Mark ................................ 417/477
2,629,333 2/1953 Olden .............................. 417/477
2,958,294 11/1960 Johnson ............................ 418/45

FOREIGN PATENT DOCUMENTS 2737920 3/1979 Fed. Rep. of Germany ...... 417/477
WO82/04291 12/1982 World Intel. Prop. Org. .... 417/477
2029514 3/1980 United Kingdom ................ 417/475

Primary Examiner—Richard E. Gluck
Attorney, Agent, or Firm—Antonelli, Terry & Wands

[57] ABSTRACT

An improved peristaltic pump is disclosed which comprises a plurality of peristaltic tubes which extend from a central suction port to a common discharge chamber. A spiral cam engages the tubes and closes the lumens defined thereby. The spiral cam is rotated relative to the tubes to effect pumping.

22 Claims, 6 Drawing Figures

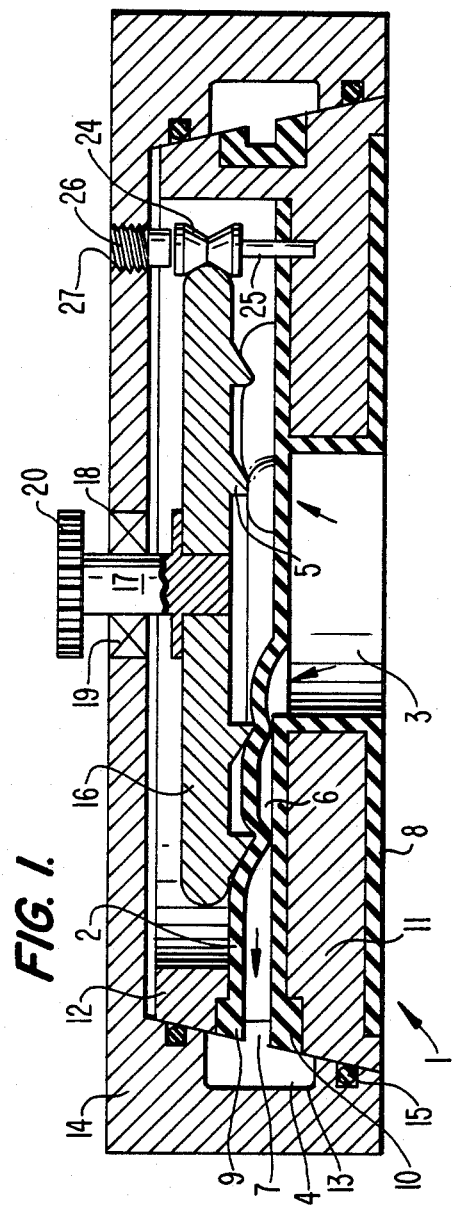
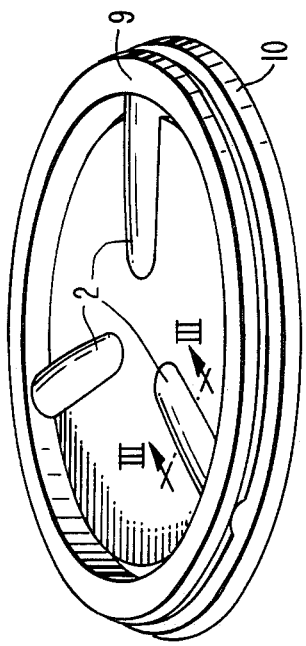
FIG. 1.
FIG. 2.

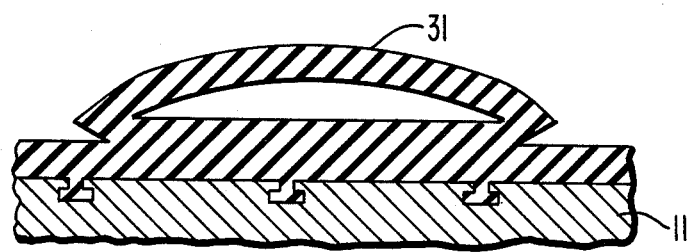
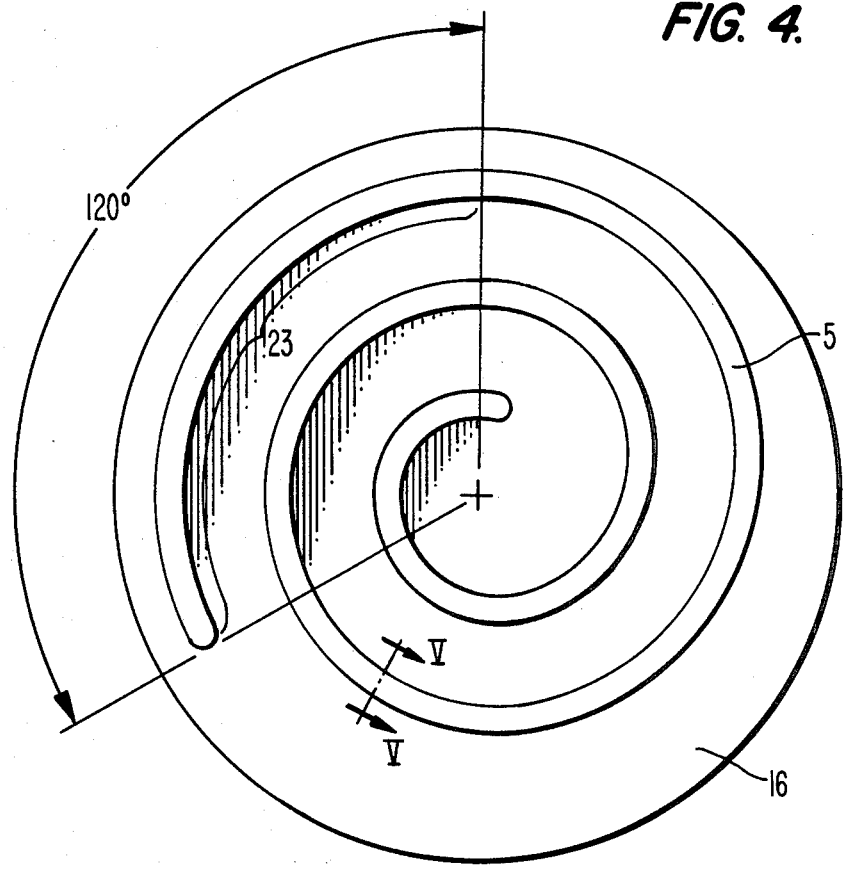

PERISTALTIC PUMP HAVING A SPIRAL CAM AND STRAIGHT PERISTALTIC TUBE

BACKGROUND AND SUMMARY OF THE INVENTION

The present invention relates to an improved peristaltic pump and method of pumping fluids. In particular, the invention is directed to a new peristaltic pump and method useful for drug infusion.

In the past, peristaltic pumps have generally been formed with a housing member defining an arcuate surface less than 360° and a resilient tubing provided in the inner radial periphery of the housing. A rotatable member having pressure elements or rollers engages the resilient tubing at spaced apart points and compresses the tubing. As the pressure elements move along the tubing, a liquid is drawn from a suction end and supplied under pressure to a discharge or supply end.

Such known peristaltic pumps present two major problems to their miniaturization and usefulness as ambulatory or implantable drug infusion devices. One of these problems is the backflow of pumped fluid due to the recovery of the peristaltic tube at its discharge end when the compressing cam or roller leaves the tube and proceeds to compress the tube at the suction end. The second problem is the high torque associated with compressing the peristaltic tube which is generally an elastomeric tube having a round cross section.

An object of the present invention is to provide an improved peristaltic pump which avoids the aforementioned problems or disadvantages associated with the known pumps so that it can be made relatively small and used as an ambulatory or implantable drug infusion device.

More specifically, an object of the present invention is to provide an improved peristaltic pump wherein the above-discussed backflow problem is overcome such that the flow discharge rate from the pump remains positive and almost constant during operation, and wherein the force associated with compressing a peristaltic tube can be minimized so that a relatively low torque is required to drive the pump.

An additional object of the invention is to provide an improved peristaltic pump having high integrity and reliability and which is characterized by a lumen which is free from undesirable creep and distortion.

These and other objects of the present invention are attained by providing a peristaltic pump comprising at least one peristaltic tube means defining a lumen extending from a suction end to a discharge end of the tube means, and an at least essentially planar, spiral cam engaging the tube means and closing the lumen thereof with at least one of the spiral cam and the tube means being rotatable relative to the other to effect pumping. This arrangement permits the pump to be relatively lightweight and compact.

In a disclosed, preferred embodiment of the invention the pump comprises a plurality of peristaltic tube means with the spiral cam engaging each of the tube means and closing the lumens thereof at a minimum of one point, and preferably two points, during the operation of the pump. According to the invention, the plurality of peristaltic tube means are formed integrally with one another by molding so as to minimize creep and distortion thereof.

More particularly, in the disclosed embodiment of the invention the peristaltic pump is formed with three peristaltic tube means whose suction ends are in fluid communication with a common suction port and whose discharge ends are in fluid communication with a common discharge chamber. The peristaltic tube means extend radially outwardly from the common suction port at equal angular spacings of 120°.

A round support member is provided for supporting the spiral cam of the pump. The support member and cam thereon are rotatable with respect to the peristaltic tube means of the pump. As an additional feature of the invention, a plurality of bearing means are provided at spaced intervals about the outer circumference of the round support member for guiding and positioning the support member and cam during rotation. Means are provided for adjusting the position of the bearing means to control the position of the support member and the spiral cam thereon with respect to the peristaltic tube means during operation of the pump. This arrangement permits an accurate adjustment of the pressure placed on the peristaltic tube means by the cam so that the tube means can be closed to prevent fluid bypassing under pressure without the application of excessive pressure which has a negative effect on required driving force and energy consumption of the device.

Further, according to the invention the cross sections of the open lumens defined by the peristaltic tube means are identical segments of a circle. Such a structure reduces the stress induced in the tube means and minimizes the compressive load needed to close the lumen thereof as compared with an elastomeric tube of round cross section. This in turn reduces the friction and the torque required to drive the device. Therefore, a smaller motor and batteries can be used with the pump thereby resulting in less weight and size.

As another feature of the invention, the end of the spiral cam which contacts the tube means adjacent the discharge end thereof during operation is extended as a cam portion having an essentially uniform radius of curvature and a height which gradually decreases so that the recovery of a peristaltic tube means adjacent the discharge end is gradual thereby minimizing the flow rate drop associated with such recovery. During this recovery all peristaltic tube means of the pump continue to deliver or discharge fluid so that the overall flow rate of the pump to the common discharge chamber remains positive and almost constant. Specifically, with an arrangement according to the disclosed, preferred embodiment having three peristaltic tube means spaced at regular intervals of 120°, the flow rate drop is inherently divided by two thirds as compared to a single peristaltic tube device.

The method of peristaltically pumping a fluid according to the invention comprises the steps of providing a source of fluid to be pumped, providing a plurality of peristaltic tube means each defining a lumen extending from a suction end in fluid communication with the source to a discharge end in fluid communication with a common discharge chamber, compressing each of the tube means at at least one point along the length thereof to close its lumen and progressively advancing the points of closure of each lumen in the direction of the discharge end of the tube means to pump fluid from the source through each of the tube means to the common discharge chamber. The moving points of closure of the lumens are at different relative positions along the lengths of the respective tube means so that the fluid discharges from the discharge ends of the tube means are out of phase with one another.

These and other objects, features and advantages of the present invention will become more apparent from the following description when taken in connection with the accompanying drawings which show, for purposes of illustration only, one preferred embodiment in accordance with the present invention.

BRIEF DESCRIPTION OF THE DRAWINGS

FIG. 1 is a schematic cross-sectional view of a peristaltic pump according to the invention;

FIG. 2 is a perspective view from slightly above and to one side of the integrally formed arrangement of peristaltic tubes with discharge ports and a common suction port;

FIG. 3 is a cross sectional view of a peristaltic tube taken along the line of III—III in FIG. 2;

FIG. 4 is a plan view taken from the underside of the spiral cam and cam plate as shown in FIG. 1;

DETAILED DESCRIPTION OF THE DISCLOSED EMBODIMENT

Figure 5:
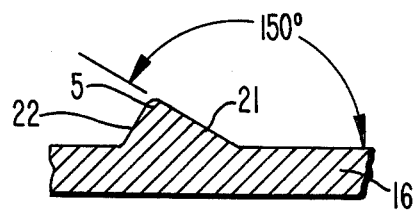
FIG. 5 is a cross-sectional view of a portion of the spiral cam and cam plate taken along the line V—V in FIG. 4.
Figure 6:
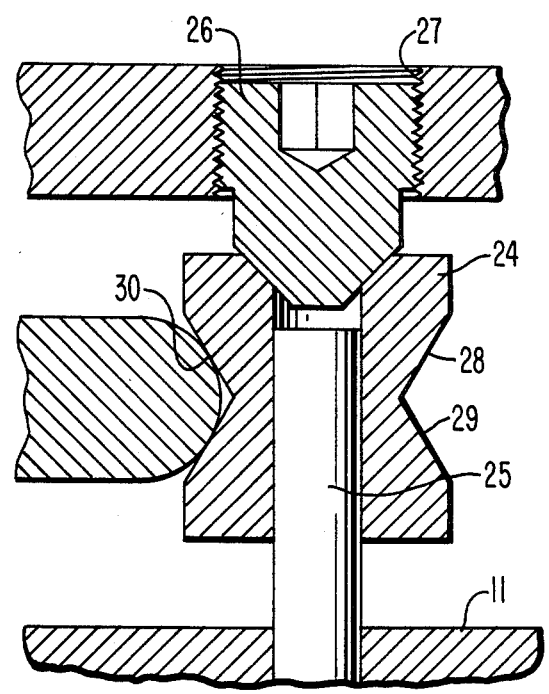
FIG. 6 is a detailed view, partially in cross-section, of a bearing supporting the spiral cam and cam plate at the peripheral edge of the cam plate as shown in FIG. 2.

Referring now to the drawings, a peristaltic pump 1 according to the invention comprises a plurality of peristaltic tube means, that is, a plurality of yieldable, preferably resilient, members such as a tubes, tube-like structures or diaphragms which can be subjected to successive waves of compression along the walls thereof to force the contents therein onward. More particularly, in the illustrated embodiment the pump 1 is formed with three peristaltic tubes 2 of like construction which extend radially outward in a single plane from a central, common suction port 3 to a surrounding common annular discharge chamber 4. The tubes 2 each define a lumen 6 which extends from a suction end to a discharge end of the tube. An essentially planar, spiral cam 5 engages the tubes 2 and closes the lumens thereof. The spiral cam 5 is mounted so as to be rotatable relative to the tubes 2 to effect pumping as discussed more fully hereinafter.

The peristaltic tubes 2 extend outwardly from the suction port 3 to the annular discharge chamber 4 at angular intervals of 120°. The lumens 6 defined by the tubes 2 have identical cross sections in the form of a segment of a circle as shown in FIG. 3. The cross section of the lumens could also be generally ellipsoid or bi-convex with the edges terminating substantially at a point. Such configurations reduce the stress induced in the tube when compressed and minimizes the compressive load needed to close the lumen of the tube as compared with a peristaltic tube of round cross section. Thus, with a tube configuration according to the invention, the friction of the cam sliding on the tube 2 and the torque required to drive the cam can be minimized which permits the use of a smaller pump motor and batteries thereby resulting in a pump with less weight and size.

The three radial discharge ports 7 of the tubes 2 are equidistantly positioned from the central suction port 3 at angular spacings of 120° where they empty into the annular discharge chamber 4. The tubes 2 are formed integrally with one another, with the suction port 3 and its radially extending lower flange 8 and also with annular flanges 9 and 10 at the discharge ends of the tubes. This integral structure is preferably molded in situ about a tube support member 11 of the pump. Such a construction is particularly advantageous in providing totally supported lumens free from creep or distortion thereby enabling the pump to have a high structural integrity and reliability of performance.

The tube support member 11 has an upwardly extending flange 12 at its outer periphery which supportingly receives the annular flanges 9 and 10 at the discharge ends of the tubes and which, together with a cavity 13 in the pump housing 14 defines the annular discharge chamber 4. Suitable seals such as o-rings 15 ensure that the discharge from the chamber 4 occurs only at the desired ports (not shown). The integral structure of peristaltic tubes 2, suction port 3, and flanges 8, 9 and 10 is preferably a molded elastomeric material such as polyurethane or Silastic. The tube support member 11 and pump housing 14 are formed of metal although other materials, such as a rigid plastic material may be employed.

The upper curved portions 31 of the tubes 2 are presented to the spiral actuating cam 5 which is rotated about its axis as discussed below so as to progressively move the points of closure of the lumens toward the discharge end of the tubes thereby creating a vacuum or depression at the suction ends and driving the fluid in the tubes radially outward to the discharge ends of the tubes and the common annular discharge chamber 4. The spiral cam 5 is attached to or formed integrally with a round cam support member or plate 16 which, in turn, is mounted for rotation about its central axis on a drive shaft 17. The plate 16 and spiral cam 5 are formed of metal but other materials, such as a rigid plastic material could be used. The working surface of the cam 5 is coated with Teflon to minimize sliding friction against the tubes 2. A suitable lubricant is also applied to the outer surfaces of the upper curved portions 31 of the tubes 2 for this purpose.

The upper end of the drive shaft 17 extends out of the pump housing 14 through an opening 18 therein and is rotatably guided in the opening 18 by a synthetic jewel bearing 19. A drive pinion 20 is nonrotatably secured to the upper end of the drive shaft 17. The pinion 17 is connected by suitable drive gearing to a drive motor (not shown) of the pump. A D.C. lavet type stepping motor, for example, can be used to drive the pinion 20 via a suitable reduction gear train.

The spiral cam 5 on the cam support plate 16 spirals outwardly about the center or axis of the support plate as an Archimedes spiral so that the points of compression of the tubes move outwardly with uniform velocity as the spiral cam 5 and support plate 16 are rotated at a constant speed. The spiral cam 5 makes two complete revolutions around the support plate 16 so that during rotation of the cam and support plate all three peristaltic tubes 2 are compressed at two points. The cam 5 has a uniform height and cross section over this length. As shown in FIG. 5, the leading or outwardly directed surface 21 of the cam 5 subtends an angle of at least 150° with the plane of the support plate 16 so that the peristaltic tubes 2 are progressively compressed to the point of lumen closure when the cam and plate are rotated. The top of the cam 5 as shown in FIG. 5 is rounded at its crest and is provided with a more steeply inclined trailing surface 22. The height of the cam 5 is sufficient to effect closure of the peristaltic tubes 2 with a clearance remaining between the uncompressed or open portions of the tubes and the lower surface of the support plate 16. The inner end of the spiral cam is located just slightly radially inwardly of the beginning of the curved portions 31 of the tubes 2 so over an angle of 120° or less, the cam spirals outwardly and contacts a tube 2 and closes the lumen thereof.

The radially outer end of the spiral cam 5 adjacent the discharge end of the peristaltic tubes 2 is extended as a cam portion 23 having an essentially uniform radius of curvature about the axis of the spiral cam and support plate 16. The height of the cam portion 23 also gradually decreases over the length of the cam portion. As shown in FIG. 4, the cam portion 23 subtends an angle of 120°. The recovery of the peristaltic tubes 2 adjacent the discharge end is therefore gradual which, in turn, minimizes the effect of the backflow into the recovering peristaltic tube on the overall flow rate of the pump. More specifically, since the tube recovery occurs simultaneously with the advancing of a radially inward point of closure on the same tube, fluid is continuously pumped toward the discharge end of the tube during recovery. Because of this and the three tube arrangement, discharge flow rate variations are virtually eliminated with the pump of the invention.

The round cam support plate 16 is located above the peristaltic tubes 2 and suction port 3 so that its axis is aligned with that of the center of the annular, integrally molded structure of the tubes and suction port. While the synthetic jewel bearing 19 in the pump housing 14 laterally positions the drive shaft 17 of support plate 16 and cam 5, the shaft 17 is free to slide relative to the bearing in a direction along its longitudinal axis. Three sapphire jewel bearings 24 are spaced uniformly about the circumference of the support plate 16. The bearings 24 are mounted on posts 25 connected to the tube support member 11 so that they can float downward and rotate on the posts. Adjustment screws 26 provided in threaded openings 27 of the pump housing 14 limit the upward movement of the bearings on the posts. Inwardly tapered surfaces 28 and 29 of the bearings engage the rounded, outer peripheral edge 30 of the cam support plate 16 to guide the support plate and cam thereon during rotation and to limit the vertical position or spacing of the support plate and spiral cam with respect to the peristaltic tubes 2. The position of the bearings 24 can be adjusted by means of the adjustment screws 26 to optimize the compression of the tubes 2 by the spiral cam. In particular, it is desirable to close the tubes 2 to prevent bypassing under pressure without the application of excessive pressure to the tube which has a negative effect on energy consumption of the device.

In the operation of the peristaltic pump 1 and according to the method of the invention, a fluid such as a liquid drug, for example insulin, is provided in the area of the suction port 3 of the pump. The plurality of peristaltic tubes 2 are engaged by the cam 5 to close the lumens thereof while the cam is rotated relative to the tubes so that the points of closure of the lumens are progressively advanced in the direction of the discharge ends of the tubes to pump fluid from the suction port through each tube to the common discharge chamber. The moving points of closure of the lumens are at different relative positions along the lengths of the respective tubes so that the fluid discharges from the discharge ends of the tubes are out of phase with one another. In particular, because the three peristaltic tubes 2 are spaced 120° apart, the pump of the invention inherently divides the flow rate drop by ⅔ as compared with a single tube device. Thus, the problem of backflow is avoided because two of the peristaltic tubes are pumping while the third is recovering at its discharge end. Moreover, since the recovering tube actually continues to pump fluid during recovery because of the advancement of another point of closure therein, the flow rate of the pump remains positive and almost constant at all times. With the pump of the invention it is also possible to minimize the torque required to rotate the spiral cam because of the specific configuration of the elastomeric peristaltic tubes and also the arrangement for precisely adjusting the position of the bearings 24 as discussed above.

While I have shown and described only one embodiment in accordance with the present invention, it is understood that the same is not limited thereto but is susceptible to numerous changes and modifications as known to those skilled in the art. Therefore, I do not wish to be limited to the details shown and described herein, but intend to cover all such changes and modifications as are encompassed by the scope of the appended claims.

I claim:

1. A peristaltic pump comprising at least one peristaltic tube means defining a lumen extending from a suction end to a discharge end of said tube means, and an at least essentially planar, spiral cam engaging said tube means and closing said lumen, at least one of said spiral cam and said tube means being rotatable relative to the other to effect pumping.

2. A peristaltic pump according to claim 1, wherein said peristaltic tube means extends in a direction transverse to said spiral cam.

3. A peristaltic pump according to claim 2, wherein said peristaltic tube means extends in a radial direction with respect to said spiral cam.

4. A peristaltic pump according to claim 1, wherein a plurality of said peristaltic tube means are provided, said spiral cam engaging each of said tube means and closing the lumen thereof.

5. A peristaltic pump according to claim 4, wherein said spiral cam closes each tube means at a minimum of one point during operation of said pump.

6. A peristaltic pump according to claim 5, wherein said spiral cam closes each tube means at two points during operation of said pump.

7. A peristaltic pump according to claim 4, wherein said plurality of said peristaltic tube means are formed integrally with one another by molding so as to minimize creep and distortion thereof during operation.

8. A peristaltic pump according to claim 4, wherein three peristaltic tube means are provided.

9. A peristaltic pump according to claim 4, wherein the suction ends of said plurality of peristaltic tube means are in fluid communication with a common suction port.

10. A peristaltic pump according to claim 9, wherein said plurality of peristaltic tube means extend radially outwardly from said common suction port.

11. A peristaltic pump according to claim 10, wherein three peristaltic tube means extend radially outwardly from the common suction port at angular spacings of 120°.

12. A peristaltic pump according to claim 4, wherein the discharge ends of said plurality of peristaltic tube means are in fluid communication with a common discharge chamber.

13. A peristaltic pump according to claim 12, wherein said common discharge chamber is annular and said plurality of peristaltic tube means extend radially inwardly from said annular discharge chamber.

14. A peristaltic pump according to claim 1, wherein a round support member is provided for supporting said spiral cam, said support member and said cam being rotatable with respect to said tube means.

15. A peristaltic pump according to claim 14, wherein bearing means are provided at the outer circumference of said support member for guiding the support member and cam during rotation.

16. A peristaltic pump according to claim 15, wherein means are provided for adjusting the position of said bearing means to control the position of said support member and said spiral cam thereon with respect to said tube means.

17. A peristaltic pump according to claim 1, wherein the end of said spiral cam which comes closest to the discharge end of said tube means during operation is extended as a cam portion having an essentially uniform radius of curvature.

18. A peristaltic pump according to claim 1, wherein the cross section of the open lumen defined by said peristaltic tube means is a segment of a circle.

19. A peristaltic pump according to claim 1, wherein said peristaltic tube means is formed from an elastomeric material.

20. A peristaltic pump according to claim 1, wherein the spiral of said cam is an Archimedes spiral.

21. A peristaltic pump comprising a central suction port, an annular discharge chamber surrounding said suction port in spaced relationship thereto, three peristaltic tubes extending outwardly from said suction port to said annular discharge chamber at angular intervals of approximately 120°, each of said tubes defining a lumen extending from a suction end to a discharge end of the tube, and a rotatable spiral cam engaging each of said tubes and closing the lumen thereof.

22. A method of peristaltically pumping a fluid comprising the steps of providing a source of fluid to be pumped, providing at least one peristaltic tube means defining a lumen extending from a suction end in fluid communication with said source to a discharge end of said tube means, engaging said tube means with an at least essentially planar, spiral cam to compress said tube means at at least one point along the length thereof to close its lumen and effecting relative rotational movement between said tube means and said cam to progressively advance the point of closure of the lumen in the direction of the discharge end of the tube means to pump fluid from said source through said tube means.

* * * * *